(12) United States Patent
Tenn, III (10) Patent No.: US 9,133,226 B2
(45) Date of Patent: *Sep. 15, 2015

(54) EXTRACTION SOLVENT CONTROL FOR REDUCING STABLE EMULSIONS

(71) Applicant: INVISTA North America S.a.r.l., Wilmington, DE (US)

(72) Inventor: William J. Tenn, III, Beaumont, TX (US)

(73) Assignee: INVISTA North America S.a.r.l., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/367,159

(22) PCT Filed: Nov. 20, 2012

(86) PCT No.: PCT/US2012/065973
§ 371 (c)(1),
(2) Date: Jun. 19, 2014

(87) PCT Pub. No.: WO2013/095852
PCT Pub. Date: Jun. 27, 2013

(65) Prior Publication Data
US 2014/0316153 A1  Oct. 23, 2014

Related U.S. Application Data

(60) Provisional application No. 61/578,524, filed on Dec. 21, 2011.

(51) Int. Cl.
| | |
|---|---|
| *C07F 15/04* | (2006.01) |
| *C07F 9/141* | (2006.01) |
| *C07F 9/6574* | (2006.01) |
| *B01D 11/04* | (2006.01) |
| *B01J 31/18* | (2006.01) |
| *B01J 31/26* | (2006.01) |
| *B01J 31/40* | (2006.01) |
| *C07F 9/145* | (2006.01) |

(52) U.S. Cl.
CPC .......... *C07F 15/045* (2013.01); *B01D 11/0426* (2013.01); *B01D 11/0457* (2013.01); *B01J 31/185* (2013.01); *B01J 31/26* (2013.01); *B01J 31/4053* (2013.01); *C07F 9/141* (2013.01); *C07F 9/145* (2013.01); *C07F 9/65746* (2013.01)

(58) Field of Classification Search
CPC ...... C07F 9/145; C07F 9/65746; B01J 31/22; B01J 2231/322; B01D 11/0426; B01D 11/0457
USPC .......................................... 556/13; 558/147
See application file for complete search history.

(56) References Cited

U.S. PATENT DOCUMENTS

| | | | |
|---|---|---|---|
| 3,325,255 A | 6/1967 | Treybal | |
| 3,374,988 A | 3/1968 | Eckert | |
| 3,479,378 A | 11/1969 | Orlandini et al. | |
| 3,496,215 A | 2/1970 | Drinkard et al. | |
| 3,496,217 A | 2/1970 | Drinkard | |
| 3,496,218 A | 2/1970 | Drinkard | |
| 3,773,809 A | 11/1973 | Walter | |
| 4,080,374 A | 3/1978 | Corn | |
| 4,082,811 A | 4/1978 | Shook, Jr. | |
| 4,290,880 A | 9/1981 | Leonard et al. | |
| 4,339,395 A | 7/1982 | Barnette et al. | |
| 4,385,007 A | 5/1983 | Shook | |
| 4,387,056 A | 6/1983 | Stowe | |
| 4,539,302 A | 9/1985 | Leyendecker | |
| 4,551,314 A | 11/1985 | Beckstead et al. | |
| 4,990,645 A | 2/1991 | Back | |
| 5,512,695 A | 4/1996 | Kreutzer et al. | |
| 5,512,696 A | 4/1996 | Kreutzer et al. | |
| 5,523,453 A | 6/1996 | Breikss | |
| 5,543,536 A | 8/1996 | Tam | |
| 5,663,369 A | 9/1997 | Kreutzer et al. | |
| 5,688,986 A | 11/1997 | Tam et al. | |
| 5,693,843 A | 12/1997 | Breikss et al. | |
| 5,723,641 A | 3/1998 | Tam et al. | |
| 5,847,101 A | 12/1998 | Okayama et al. | |
| 5,879,556 A | 3/1999 | Hein | |
| 5,959,135 A | 9/1999 | Garner et al. | |
| 6,120,700 A | 9/2000 | Foo et al. | |
| 6,171,996 B1 | 1/2001 | Garner et al. | |
| 6,171,997 B1 | 1/2001 | Foo et al. | |
| 6,262,145 B1 | 7/2001 | Winjngaarden et al. | |
| 6,294,700 B1 | 9/2001 | Kanel | |
| 6,303,829 B1 | 10/2001 | Kanel et al. | |

(Continued)

FOREIGN PATENT DOCUMENTS

| | | |
|---|---|---|
| DE | 102004045036 A1 | 3/2006 |
| GB | 835282 A | 5/1960 |

OTHER PUBLICATIONS

International Search Report and Written Opinion issued in corresponding PCT/US2014/043134 on Sep. 12, 2014.
International Search Report and Written Opinion issued in related PCT/US2014/043125 on Sep. 12, 2014.
International Search Report and Written Opinion issued in related PCT/US2014/043132 on Sep. 12, 2014.
International Search Report and Written Opinion issued in related PCT/US2014/04394 on Sep. 10, 2014.

*Primary Examiner* — Porfirio Nazario Gonzalez
(74) *Attorney, Agent, or Firm* — Robert B. Furr, Jr.; Edward F. Kenehan, Jr.

(57) ABSTRACT

Disclosed herein are methods for recovering diphosphite-containing compounds from mixtures comprising organic mononitriles and organic dinitriles, using liquid-liquid extraction. Also disclosed are pre-treatments to enhance extractability of the diphosphite-containing compounds.

18 Claims, 1 Drawing Sheet

(56) References Cited

U.S. PATENT DOCUMENTS

| | | |
|---|---|---|
| 6,310,260 B1 | 10/2001 | Argyropoulos et al. |
| 6,399,534 B2 | 6/2002 | Bunel et al. |
| 6,469,194 B2 | 10/2002 | Burattin |
| 6,478,965 B1 | 11/2002 | Holtzapple et al. |
| 6,770,770 B1 | 8/2004 | Baumann et al. |
| 6,924,345 B2 | 8/2005 | Gagne et al. |
| 6,936,171 B2 | 8/2005 | Jackson et al. |
| 7,084,294 B2 | 8/2006 | Jungkamp |
| 7,528,275 B2 | 5/2009 | Bartsch |
| 7,541,486 B2 | 6/2009 | Scheidel |
| 7,612,223 B2 | 11/2009 | Rosier |
| 7,659,422 B2 | 2/2010 | Foo |
| 7,705,171 B2 | 4/2010 | Haderlein et al. |
| 7,709,673 B2 | 5/2010 | Foo |
| 7,709,674 B2 | 5/2010 | Foo |
| 7,781,608 B2 | 8/2010 | Scheidel |
| 7,816,551 B2 | 10/2010 | Jungkamp |
| 7,880,028 B2 | 2/2011 | Foo |
| 7,897,801 B2 | 3/2011 | Rosier |
| 7,935,229 B2 | 5/2011 | Deckert et al. |
| 2006/0264651 A1 | 11/2006 | Bartsch |
| 2008/0076944 A1 | 3/2008 | Bartsch |
| 2008/0083607 A1 | 4/2008 | Deckert et al. |
| 2008/0207945 A1 | 8/2008 | Dee-Noor et al. |
| 2008/0281119 A1 | 11/2008 | Scheidel et al. |
| 2008/0281120 A1 | 11/2008 | Jungkamp |
| 2009/0182164 A1 | 7/2009 | Foo |
| 2009/0259034 A1 | 10/2009 | Kerr et al. |
| 2009/0270645 A1 | 10/2009 | Haderlain |
| 2010/0125151 A1 | 5/2010 | Amey |
| 2014/0316153 A1 | 10/2014 | Tenn |
| 2014/0350280 A1 | 11/2014 | Tenn |
| 2014/0364638 A1 | 12/2014 | Tenn |
| 2014/0378693 A1 | 12/2014 | Tenn |

EXTRACTION SOLVENT CONTROL FOR REDUCING STABLE EMULSIONS

RELATED APPLICATION

This application claims benefit to Provisional Application No. 61/578,524 filed Dec. 21, 2011 which is herein incorporated by reference in its entirety.

FIELD OF THE INVENTION

The invention relates to recovery of catalyst and ligand from a hydrocyanation reaction product mixture comprising organic dinitriles using liquid-liquid extraction.

BACKGROUND OF THE INVENTION

It is well known in the art that complexes of nickel with phosphorous-containing ligands are useful as catalysts in hydrocyanation reactions. Such nickel complexes using monodentate phosphites are known to catalyze hydrocyanation of butadiene to produce a mixture of pentenenitriles. These catalysts are also useful in the subsequent hydrocyanation of pentenenitriles to produce adiponitrile, an important intermediate in the production of nylon. It is further known that bidentate phosphite and phosphinite ligands can be used to form nickel-based catalysts to perform such hydrocyanation reactions.

U.S. Pat. No. 3,773,809 describes a process for the recovery of Ni complexes of organic phosphites from a product fluid containing organic nitriles produced by hydrocyanating an ethylenically unsaturated organic mononitrile such as 3-pentenenitrile through extraction of the product fluid with a paraffin or cycloparaffin hydrocarbon solvent. Similarly, U.S. Pat. No. 6,936,171 to Jackson and McKinney discloses a process for recovering diphosphite-containing compounds from streams containing dinitriles.

U.S. Pat. No. 4,339,395 describes the formation of an interfacial rag layer during extended periods of continuous extraction of certain phosphite ligands. The '395 patent notes that the interfacial rag hinders, if not halts, the phase separation. Because the process is operated continuously, the rag must be removed continuously from the interface as it accumulates to avoid interrupting operation. To solve this problem for the disclosed components, the '395 patent discloses the addition of minor amounts of substantially water-free ammonia.

SUMMARY OF THE INVENTION

This process recovers diphosphite-containing compounds from a mixture comprising diphosphite-containing compounds, organic mononitriles and organic dinitriles.

Disclosed is a process for recovering diphosphite-containing compounds from a feed mixture comprising diphosphite-containing compounds, organic mononitriles, organic dinitriles and a Lewis acid in a multistage countercurrent liquid-liquid extractor with extraction solvent comprising aliphatic hydrocarbon, cycloaliphatic hydrocarbon or a mixture of aliphatic and cycloaliphatic hydrocarbon. The process comprises:

a) flowing the feed mixture to a mixing section of a mixer-settler in the first stage of the multistage countercurrent liquid-liquid extractor;
b) contacting the feed mixture with extraction solvent from the second stage of the multistage countercurrent liquid-liquid extractor in the mixing section of the mixer-settler of the first stage to form a mixed phase comprising a light phase and a heavy phase, wherein the light phase comprises extraction solvent and extracted diphosphite-containing compounds, and wherein the heavy phase comprises organic mononitriles and organic dinitriles;
c) passing the mixture from step (b) to a settling section in the mixer-settler of the first stage, wherein the mixed phase separates into the light phase and the heavy phase; and
d) introducing a Lewis base into the settling section of the first stage, wherein a complex of Lewis acid and Lewis base is formed in the settling section in the mixer-settler of the first stage, wherein at least a portion of the light phase is withdrawn from the settling section and treated to recover diphosphite-containing compounds extracted into the light phase, wherein at least a portion of the heavy phase is passed to the second stage of the multistage countercurrent liquid-liquid extractor.

The mixing sections of the stages of the multistage countercurrent liquid-liquid extractor form an intimate mixture of unseparated light and heavy phase. This intimate mixture comprises an emulsion phase. The emulsion phase may or may not comprise particulate solid material. This emulsion phase separates into a light phase and a heavy phase in the settling sections of the stages, including the first stage. Accordingly, the settling sections of the stages will contain at least some emulsion phase located between the upper light phase and the lower heavy phase. This emulsion phase tends to reduce in size over time. However, in some instances settling takes longer than desired or the emulsion phase never fully separates into a light phase and a heavy phase. This separation problem may be particularly troublesome in the first stage of a multistage countercurrent liquid-liquid extractor.

Addition of Lewis base to the settling section of the first stage has been found to result in enhanced settling of the emulsion phase. For example, this addition may result in the reduction of the size of the emulsion phase in the settling section, wherein the size of the emulsion phase is based upon the size of the emulsion phase in the absence of addition of Lewis base. Enhanced settling in the settling section may also be measured as an increased rate of settling, based upon the rate of settling in the absence of addition of Lewis base.

Another problem, which may be solved by addition of Lewis base is formation of rag and build-up of a rag layer in the settling section. Rag formation is discussed in U.S. Pat. No. 4,339,395 and U.S. Pat. No. 7,935,229. Rag comprises particulate solid material, and may be considered to be a form of an emulsion phase, which is particularly stable in the sense that it does not dissipate in a practical amount of time for conducting an extraction process. Rag may form in the mixing section or the settling section of an extraction stage, particularly the first stage of a multistage countercurrent liquid-liquid extractor. In the settling section, the rag forms a layer between the heavy phase and the light phase. The formation of a rag layer in the settling section inhibits proper settling of the heavy phase and the light phase. The formation of a rag layer may also inhibit the extraction of diphosphite-containing compounds from the heavy phase into the light phase. In a worst case scenario, rag can build up to extent of completely filling a separation section, necessitating shut down of the extraction process to clean out the settling section. It has been found that addition of Lewis base to the settling section may reduce or eliminate the size of a rag layer or reduce its rate of formation, based upon the size and rate of formation of the rag layer in the absence of addition of Lewis base.

Accordingly, addition of Lewis base to the settling section of the first stage of a multistage countercurrent extractor may achieve at least one of the following results: (a) a reduction in the size of an emulsion phase in the settling section, based upon the size of the emulsion phase in the absence of addition of Lewis base; (b) an increase in the rate of settling in the settling section, based upon the rate of settling in the absence of addition of Lewis base; (c) an increase in the amount of diphosphite-containing compounds in the light phase, based upon the upon the amount of diphosphite-containing compounds in the light phase in the absence of addition of Lewis base; (d) a partial or total reduction in the size of a rag layer in the settling section, based upon the size of a rag layer in the settling section in the absence of addition of Lewis base; and (e) reduction in the rate of formation of a rag layer in the settling section, based upon the rate of formation of a rag layer in the settling section in the absence of addition of Lewis base.

A particular example of a Lewis acid, which may be present in the feed to the extractor, is $ZnCl_2$.

The extraction solvent feed from the second stage of the multistage countercurrent liquid-liquid extractor to the first stage of the multistage countercurrent liquid-liquid extractor may comprise at least 1000 ppm, for example, from 2000 to 5000 ppm, of diphosphite-containing compounds. The extraction solvent feed from the second stage may comprise at least 10 ppm, for example, from 20 to 200 ppm, of nickel.

The diphosphite-containing compound may be a diphosphite ligand selected from the group consisting of:

$(R^1O)_2P(OZO)P(OR^1)_2$,  I

II

III and
wherein in I, II and III, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and wherein Z and $Z^1$ are independently selected from the group consisting of structural formulae IV, V, VI, VII, and VIII:

IV

V and wherein
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy;
X is O, S, or $CH(R^{10})$;
$R^{10}$ is H or $C_1$ to $C_{12}$ alkyl;

VI

VII and wherein
$R^{11}$ and $R^{12}$ are independently selected from the group consisting of H, $C_1$ to $C_{12}$ alkyl, and $C_1$ to $C_{12}$ alkoxy and $CO_2R^{13}$,
$R^{13}$ is $C_1$ to $C_{12}$ alkyl, or $C_6$ to $C_{10}$ aryl unsubstituted or substituted with $C_1$ to $C_4$ alkyl;
Y is O, S, or $CH(R^{14})$;
$R^{14}$ is H or $C_1$ to $C_{12}$ alkyl;

VIII wherein
$R^{15}$ is selected from the group consisting of H, $C_1$ to $C_{12}$ alkyl, and $C_1$ to $C_{12}$ alkoxy and $CO_2R^{16}$,
$R^{16}$ is $C_1$ to $C_{12}$ alkyl, or $C_6$ to $C_{10}$ aryl, unsubstituted or substituted with $C_1$ to $C_4$ alkyl,
and wherein
for structural formulae I through VIII, the $C_1$ to $C_{12}$ alkyl, and $C_1$ to $C_{12}$ alkoxy groups may be straight chain or branched.

At least a portion of the diphosphite ligand may be complexed with zero valent Ni.

At least one stage of the extraction may be carried out above 40° C.

The Lewis base may be a monodentate triarylphosphite, wherein the aryl groups are unsubstituted or substituted with alkyl groups having 1 to 12 carbon atoms, and wherein the aryl groups may be interconnected.

The Lewis base may optionally be selected from the group consisting of:
a) anhydrous ammonia, pyridine, alkylamine, dialkylamine, trialkylamine wherein the alkyl groups have 1 to 12 carbon atoms; and
b) polyamine.

If the Lewis base is a polyamine, the polyamine may comprise at least one selected from hexamethylene diamine, and dimers and trimers of hexamethylene diamine, for example, bis-hexamethylene triamine.

The Lewis base may optionally comprise a basic ion exchange resin, for example, Amberlyst 21® resin.

One example of a suitable cyclic alkane extraction solvent is cyclohexane.

The feed mixture may be an effluent stream from a hydrocyanation process, for example, a process for hydrocyanating 3-pentenenitrile, a process for the single hydrocyanation of 1,3-butadiene to pentenenitriles or a process for the double hydrocyanation of 1,3-butadiene to adiponitrile.

DETAILED DESCRIPTION OF THE INVENTION

The processes of the present invention involve methods for recovering diphosphite-containing compounds from a mixture comprising diphosphite-containing compounds and organic dinitriles, using liquid-liquid extraction.

Figure 1:
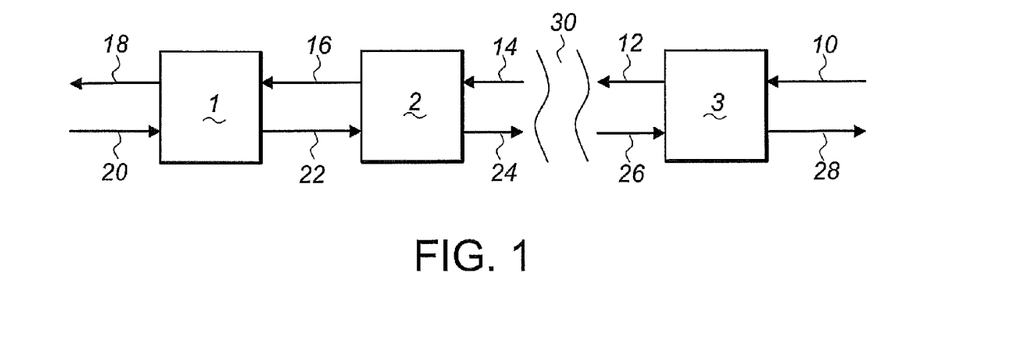
FIG. 1 is a diagram showing the flow of fluids through a multistage countercurrent liquid-liquid extractor.

FIG. 1 is a diagram of a multistage countercurrent liquid-liquid extractor. Lines in FIG. 1 represent flow of materials, rather than any particular type of equipment, such as pipes. Similarly, squares in this diagram represent stages or sections for mixing and settling, rather than any particular type of equipment.

Three stages are depicted in FIG. 1. The first stage is depicted by mixing and settling section 1. The second stage is depicted by mixing and settling section 2. The final stage is depicted by mixing and settling section 3. Gap 30 represents a space where additional stages may be inserted. For example, one or more, for example, from one to four, mixing and settling sections may be inserted in gap 30 between mixing and settling section 2 and mixing and settling section 3.

In FIG. 1, a fresh extraction solvent feed, for example, cyclohexane, is introduced into the multistage countercurrent extractor via line 10. The extraction solvent or light phase exiting from mixing settling section 3 passes through line 12 to the next stage of the multistage extractor. In a multistage countercurrent liquid-liquid extractor having three stages, extraction solvent in line 12 would pass directly into stage 2 via line 14. Extraction solvent from stage 2 passes through line 16 to stage 1. The extraction solvent comprising extracted diphosphite-containing compounds passes out of the stage 1 mixing and settling section through line 18.

A feed comprising diphosphite-containing compounds is fed into the stage 1 mixer and settler via line 20. The feed further comprises a mixture comprising organic mononitriles and dinitriles, which is immiscible with the extraction solvent. The feed further comprises a Lewis acid. In stage 1, a portion of the diphosphite-containing compounds is extracted into the extraction solvent which exits stage 1 via line 18. The immiscible dinitrile and mononitrile mixture or the heavy phase is removed from the stage 1 mixing and settling section by line 22 and is passed into the stage 2 mixing and settling section. A portion of the diphosphite-containing compounds is extracted into the light phase in the stage 2 mixing and settling section. The heavy phase exits the stage 2 mixing and settling section by line 24. Similarly, if there are additional stages in gap 30 shown in FIG. 1, extraction of diphosphite-containing compounds will take place in such intermediate stages in a similar manner to that taking place in stage 2.

After the heavy phase passes through the first stage and any intermediate stages, it passes through the final stage mixing and settling section 3. In particular, the heavy phase is introduced into mixing and setting section 3 through line 26. After passing through the final stage mixing and settling section 3, the heavy phase exits via line 28.

A two-stage multistage countercurrent liquid-liquid extractor is represented in FIG. 1 by mixing and settling sections 1 and 2; lines 14, 16 and 18 showing the direction of extraction solvent flow; and lines 20, 22 and 24 showing the direction of heavy phase flow. In a two-stage multistage counter current liquid-liquid extractor, mixing and settling section 3; lines 10, 12, 26 and 28; and gap 30 are omitted. In the two stage countercurrent liquid-liquid extractor, extraction solvent comprising extracted diphospite-containing compounds passes from the extractor through line 18, and extracted heavy phase, i.e. raffinate, passes from the extractor through line 24.

Thus, it can be seen that the multistage countercurrent liquid-liquid extractor comprises two or more stages with countercurrent flow of extraction solvent and heavy phase. In view of the direction of flow of light and heavy phase through the stages of extraction, it will be appreciated that the concentration of solute, e.g., diphosphite-containing compound, is highest in both the light and heavy phases of the first stage and lowest in the light and heavy phases of the final stage.

Figure 2:
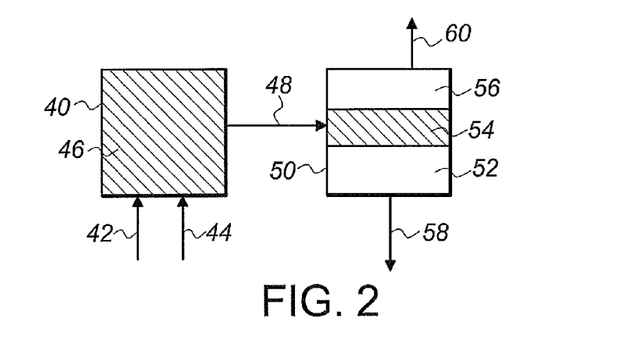
FIG. 2 is a diagram showing a mixing section and a settling section of a stage of a multistage countercurrent liquid-liquid extractor.

FIG. 2 is a diagrammatic representation of one type of a mixing and settling section, also referred to herein as a mixer-settler. This type of mixer-settler may be used in any of the stages shown in FIG. 1. This mixer-settler comprises a mixing section 40 and a settling section 50. The mixing section 40 and the settling section 50 are separate. All of the effluent from the mixing section 40 flows into the settling section 50. Fluid from the mixing section 40 flows through the settling section 50 in a in a horizontal manner, although there is also no restriction of movement of fluids vertically throughout the settling section 50.

An extraction solvent is introduced into the mixing section 40 by line 42. A feed comprising diphosphite-containing compounds is introduced into the mixing section 40 by line 44. Alternatively, the contents of lines 42 and 44 may be combined upstream of the mixing section 40 and introduced into mixing section 40 through a single inlet. These two feeds are mixed in the mixing section 40 to provide a mixed phase comprising an emulsion phase represented in FIG. 2 by shaded area 46.

Line 48 represents the flow of mixed phase 46 from the mixing section 40 into the settling section 50. As depicted in FIG. 2, there are three phases in the settling section 50, including a heavy phase 52, a mixed phase 54, and a light phase 56. The heavy phase 52 is depleted in diphosphite-containing compounds, insofar as it has a lower concentration of diphosphite-containing compounds as compared with the concentration of diphosphite-containing compounds in feed 44, due to the extraction of diphosphite-containing compounds into the light phase 56. Correspondingly, the light phase 56 is enriched in diphosphite-containing compounds, insofar as it has a higher concentration of diphosphite-containing compounds as compared with the concentration of diphosphite-containing compounds in extraction solvent feed 42, due to the extraction of diphosphite-containing compounds into the light phase 56. At least a portion of the heavy phase 52 exits the settling section 50 via line 60. At least a portion of the light phase 56 is removed from the settling section 50 via line 58.

Although not shown in FIG. 2, which is diagrammatically shows the flow of fluids, it will be understood that each of the mixing section 40 and the settling section 50 may comprise one or more stages, subsections, compartments or chambers. For example, settling section 50 may include more than one chamber between the point of introduction of the mixed phase 46 through line 48 and the point of withdrawal of light phase and heavy phase through lines 58 and 60. Horizontal extension between the point of introduction of the mixed phase 46 through line 48 and the point of withdrawal of light and heavy phases through lines 58 and 60 promotes settling of the light and heavy phases 56 and 52. The size of the mixed phase 54 may become progressively smaller as fluids settle and flow through the chamber. For example, the final chamber from where fluids are removed may include little or no mixed phase 54. It will further be understood that mixing section 40 may include one or more types of mixing apparatus, such as an impeller, not shown in FIG. 2.

Figure 3:
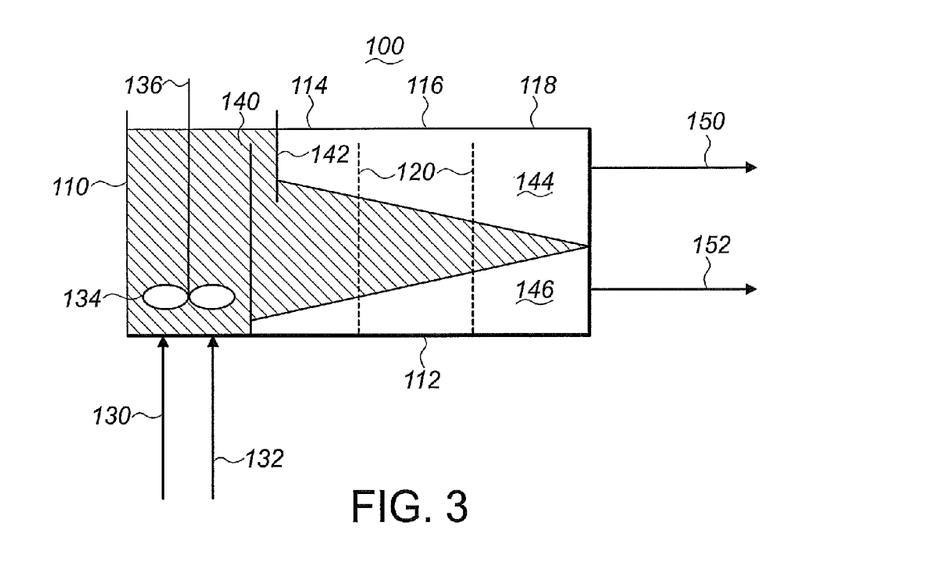
FIG. 3 is a diagram showing a mixing/settling apparatus having three chambers in the settling section.

FIG. 3 provides a representation of a mixer-settler 100 having a multistage settling section. Mixer-settler 100 has a mixing section 110 and a settling section 112. In mixer-settler 100, the mixing section 110 is separate from the settling section 112. The settling section has three compartments, represented in FIG. 3 as sections 114, 116, and 118. These sections are separated by coalescence plates 120. The coalescence plates 120 may be designed to provide flow of separated light and heavy phases between chambers, while restricting the flow of emulsion phase between chambers. A feed comprising a diphosphite-containing compound is passed into the mixing section 110 via line 130. The extraction solvent is introduced into mixing section 110 via line 132. The mixing section 110 includes an impeller 134 mounted on shaft 136 to provide for mechanical mixing of fluids. Mixing of the feeds provides a mixed phase comprising an emulsion phase represented in FIG. 3 by shading 140.

The mixed phase 140 flows into the settling section 112 as an overflow from the mixing section 110. This mixed phase 140 is prevented from flowing directly into the light phase 144 by baffle plate 142. As settling occurs in settling section 112, the volume of the mixed phase 140 decreases, the volume of the light phase 144 increases, and the volume of the heavy phase 146 increases. Heavy phase 146 is removed from settling section 112, in particular from chamber 118, via line 152 and light phase 144 is removed from settling section 112, in particular, from chamber 118, via line 150.

It is desirable for both a mononitrile and a dinitrile to be present in the countercurrent contactor. For a discussion of the role of monodentate and bidentate ligand in extraction of hydrocyanation reactor effluent streams, see U.S. Pat. No. 3,773,809 to Walter and U.S. Pat. No. 6,936,171 to Jackson and McKinney.

For the process disclosed herein, suitable molar ratios of mononitrile to dinitrile components include 0.01 to 2.5, for example, 0.01 to 1.5, for example 0.65 to 1.5.

Maximum temperature is limited by the volatility of the hydrocarbon solvent utilized, but recovery generally improves as the temperature is increased. Examples of suitable operating ranges are 40° C. to 100° C. and 50° C. to 80° C.

The controlled addition of monophosphite ligands may enhance settling. Examples of monophosphite ligands that may be useful as additives include those disclosed in Drinkard et al U.S. Pat. No. 3,496,215, U.S. Pat. No. 3,496,217, U.S. Pat. No. 3,496,218, U.S. Pat. No. 5,543,536, and published PCT Application WO 01/36429 (BASF).

As disclosed herein, the addition of Lewis base compounds to a mixture comprising diphosphite-containing compounds, organic mononitriles and organic dinitriles enhances settling, especially when the mixture comprises a Lewis acid, such as $ZnCl_2$. Examples of suitable weak Lewis base compounds include water and alcohols. Suitable stronger Lewis base compounds include hexamethylene diamine, dimers and trimers of hexamethylene diamine, ammonia, aryl- or alkyl amines, such as pyridine or triethylamine, or basic resins such as Amberlyst 21®, a commercially available basic resin made by Rohm and Haas. The addition of Lewis base may reduce or eliminate any inhibiting effect of Lewis acid on catalyst recovery.

The reaction product of Lewis acid with Lewis base may become entrailed in the raffinate phase as it moves through the multistage countercurrent liquid-liquid extractor. In particular, this product may form a precipitate in the raffinate phase in the form of a complex of Lewis acid with Lewis base. However, this precipitate may exist as a dispersion of fine particles distributed throughout the raffinate phase. This precipitate may be removed by conventional techniques, such as filtration, centrifugation or distillation accompanied by removal of bottoms containing the precipitate, after the raffinate is removed from the last stage of the multistage countercurrent liquid-liquid extractor.

The diphosphite-containing compounds extracted by the processes described herein comprise bidentate phosphorus-containing ligands. These extracted ligands comprise free ligands (e.g., those which are not complexed to a metal, such as nickel) and those which are complexed to a metal, such as nickel. Accordingly, it will be understood that extraction processes described herein are useful for recovering diphosphite-containing compounds which are metal/ligand complexes, such as a complex of zero valent nickel with at least one ligand comprising a bidentate-phosphorus containing ligand.

Suitable ligands for extraction are bidentate phosphorous-containing ligands selected from the group consisting of bidentate phosphites, and bidentate phosphinites. Preferred ligands are bidentate phosphite ligands.

Diphosphite Ligands

Examples of bidentate phosphite ligands useful in the invention include those having the following structural formulae:

I

II

III and wherein in I, II and III, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and Z and $Z^1$ are independently selected from the group consisting of structural formulae IV, V, VI, VII, and VIII:

IV

V and wherein

$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy;

X is O, S, or $CH(R^{10})$;

$R^{10}$ is H or $C_1$ to $C_{12}$ alkyl;

VI

VII and wherein $R^{11}$ and $R^{12}$ are independently selected from the group consisting of H, $C_1$ to $C_{12}$ alkyl, and $C_1$ to $C_{12}$ alkoxy; and $CO_2R^{13}$, $R^{13}$ is $C_1$ to $C_{12}$ alkyl or $C_6$ to $C_{10}$ aryl, unsubstituted or substituted with $C_1$ to $C_4$ alkyl;

Y is O, S, or $CH(R^{14})$;

$R^{14}$ is H or $C_1$ to $C_{12}$ alkyl;

VIII wherein $R^{15}$ is selected from the group consisting of H, $C_1$ to $C_{12}$ alkyl, and $C_1$ to $C_{12}$ alkoxy and $CO_2R^{16}$;

$R^{16}$ is $C_1$ to $C_{12}$ alkyl or $C_6$ to $C_{10}$ aryl, unsubstituted or substituted with $C_1$ to $C_4$ alkyl.

In the structural formulae I through VIII, the $C_1$ to $C_{12}$ alkyl, and $C_1$ to $C_{12}$ alkoxy groups may be straight chain or branched.

Another example of a formula of a bidentate phosphite ligand that is useful in the present process is that having the Formula X, shown below

X

Further examples of bidentate phosphite ligands that are useful in the present process include those having the Formulae XI to XIV, shown below wherein for each formula, $R^{17}$ is selected from the group consisting of methyl, ethyl or isopropyl, and $R^{18}$ and $R^{19}$ are independently selected from H or methyl:

XI

XII

XIII

XIV

Additional examples of bidentate phosphite ligands that are useful in the present process include a ligand selected from a member of the group represented by Formulae XV and XVI, in which all like reference characters have the same meaning, except as further explicitly limited:

Formula XV

Formula XVI wherein $R^{41}$ and $R^{45}$ are independently selected from the group consisting of $C_1$ to $C_5$ hydrocarbyl, and each of $R^{42}$, $R^{43}$, $R^{44}$, $R^{46}$, $R^{47}$ and $R^{48}$ is independently selected from the group consisting of H and $C_1$ to $C_4$ hydrocarbyl.

For example, the bidentate phosphite ligand can be selected from a member of the group represented by Formula XV and Formula XVI, wherein $R^{41}$ is methyl, ethyl, isopropyl or cyclopentyl;
$R^{42}$ is H or methyl;
$R^{43}$ is H or a $C_1$ to $C_4$ hydrocarbyl;
$R^{44}$ is H or methyl;
$R^{45}$ is methyl, ethyl or isopropyl; and
$R^{46}$, $R^{47}$ and $R^{48}$ are independently selected from the group consisting of H and $C_1$ to $C_4$ hydrocarbyl.

As additional examples, the bidentate phosphite ligand can be selected from a member of the group represented by Formula XV, wherein $R^{41}$, $R^{44}$ and $R^{45}$ are methyl;
$R^{42}$, $R^{46}$, $R^{47}$ and $R^{48}$ are H; and
$R^{43}$ is a $C_1$ to $C_4$ hydrocarbyl;

or $R^{41}$ is isopropyl;
$R^{42}$ is H;
$R^{43}$ is a $C_1$ to $C_4$ hydrocarbyl;
$R^{44}$ is H or methyl;
$R^{45}$ is methyl or ethyl;
$R^{46}$ and $R^{48}$ are H or methyl; and
$R^{47}$ is H, methyl or tertiary-butyl;

or the bidentate phosphite ligand can be selected from a member of the group represented by Formula XVI, wherein

$R^{41}$ is isopropyl or cyclopentyl;
$R^{45}$ is methyl or isopropyl; and
$R^{46}$, $R^{47}$, and $R^{48}$ are H.

As yet another example, the bidentate phosphite ligand may be represented by Formula XV, wherein $R^{41}$ is isopropyl; $R^{42}$, $R^{46}$, and $R^{48}$ are H; and $R^{43}$, $R^{44}$, $R^{45}$, and $R^{47}$ are methyl.

It will be recognized that Formulae X to XVI are two-dimensional representations of three-dimensional molecules and that rotation about chemical bonds can occur in the molecules to give configurations differing from those shown. For example, rotation about the carbon-carbon bond between the 2- and 2'-positions of the biphenyl, octahydrobinaphthyl, and or binaphthyl bridging groups of Formulae X to XVI, respectively, can bring the two phosphorus atoms of each Formula in closer proximity to one another and can allow the phosphite ligand to bind to nickel in a bidentate fashion. The term "bidentate" is well known in the art and means both phosphorus atoms of the ligand are bonded to a single nickel atom.

Further examples of bidentate phosphite ligands that are useful in the present process include those having the formulae XX to LIII, shown below wherein for each formula, $R^{17}$ is selected from the group consisting of methyl, ethyl or isopropyl, and $R^{18}$ and $R^{19}$ are independently selected from H or methyl:

XXIV

XXVI

XXV

XXVII

XXVIII

XXX

XXIX

XXXI

XXXII

XXXIV

XXXIII

XXXV

XXXVI

XXXVII

XXXVIII

XXXIX

L

LI

LII

LIII

Additional suitable bidentate phosphites are of the type disclosed in U.S. Pat. Nos. 5,512,695; 5,512,696; 5,663,369; 5,688,986; 5,723,641; 5,847,101; 5,959,135; 6,120,700; 6,171,996; 6,171,997; 6,399,534; the disclosures of which are incorporated herein by reference. Suitable bidentate phosphinites are of the type disclosed in U.S. Pat. Nos. 5,523,453 and 5,693,843, the disclosures of which are incorporated herein by reference.

Extraction Solvent

Suitable hydrocarbon extraction solvents include paraffins and cycloparaffins (aliphatic and alicyclic hydrocarbons) having a boiling point in the range of about 30° C. to about 135° C., including n-pentane, n-hexane, n-heptane and n-octane, as well as the corresponding branched chain paraffinic hydrocarbons having a boiling point within the range specified. Useful alicyclic hydrocarbons include cyclopentane, cyclohexane and cycloheptane, as well as alkyl substituted alicyclic hydrocarbons having a boiling point within the specified range. Mixtures of hydrocarbons may also be used, such as, for example, mixtures of the hydrocarbons noted above or commercial heptane which contains a number of hydrocarbons in addition to n-heptane. Cyclohexane is the preferred extraction solvent.

The lighter (hydrocarbon) phase recovered from the multistage countercurrent liquid-liquid extractor is directed to suitable equipment to recover catalyst, reactants, etc. for recycle to the hydrocyanation, while the heavier (lower) phase containing dinitriles recovered from the multistage countercurrent liquid-liquid extractor is directed to product recovery after removal of any solids, which may accumulate in the heavier phase. These solids may contain valuable components which may also be recovered, e.g., by the process set forth in U.S. Pat. No. 4,082,811.

EXAMPLES

In the following examples, values for extraction coefficient are the ratio of weight fraction of catalyst in the extract phase (hydrocarbon phase) versus the weight fraction of catalyst in the raffinate phase (organonitrile phase). An increase in extraction coefficient results in greater efficiency in recovering catalyst. As used herein, the terms, light phase, extract phase and hydrocarbon phase, are synonymous. Also, as used herein, the terms, heavy phase, organonitrile phase and raffinate phase, are synonymous.

Analysis of the extract and the raffinate streams of the catalyst extraction was conducted on an Agilent 1100 series HPLC and via ICP. The HPLC was used to determine the extraction efficiency of the process.

Example 1

To a 50 mL, jacketed, glass laboratory extractor, equipped with a magnetic stirbar, digital stir-plate, and maintained at 65° C., was charged 10 grams of the product of a pentenenitrile-hydrocyanation reaction, and 10 grams of the extract from the second stage of a mixer-settler cascade, operated in counter-current flow. The extract from the second stage contained approximately 50 ppm nickel and 3100 ppm diphosphite ligand. No additives were present.

The reactor product was approximately:

85% by weight $C_6$ dinitriles

14% by weight $C_5$ mononitriles

1% by weight catalyst components 420 ppm by weight active nickel 566 ppm by weight zinc.

The laboratory reactor was then mixed at 1160 rotations-per-minute, for 20 minutes, and then allowed to settle for 15 minutes. After settling for 15 minutes, a stable emulsion was present throughout the extract phase. Samples were obtained of the extract and raffinate phases of the extractor and analyzed to determine the extent of catalyst extraction. The ratio of active nickel present in the extract phase vs. the raffinate phase was found to be 14. The concentration of zinc in the raffinate was 566 ppm.

Example 2

Example 1 was repeated except that 500 ppm of polyethylenimine (PEI) was added to the system. The polyethylenimine (PEI) was end-capped with ethylenediamine and had an average Mn~600.

Example 3

Example 1 was repeated except that 1000 ppm of polyethylenimine (PEI) was added to the system. The polyethylenimine (PEI) was end-capped with ethylenediamine and had an average Mn~600.

Example 4

Example 1 was repeated except that 500 ppm of polyethylenimine, aqueous solution (PEI/$H_2O$) was added to the system. The polyethylenimine, aqueous solution was a polyethylenimine solution in water having a PEI/$H_2O$ ratio of 1:1. The polyethyleneimine had an average Mn~1200.

Example 5

Example 1 was repeated except that 1000 ppm of polyethylenimine, aqueous solution (PEI/$H_2O$) was added to the system. The polyethylenimine, aqueous solution was a polyethylenimine solution in water having a PEI/$H_2O$ ratio of 1:1. The polyethyleneimine had an average Mn~1200.

Example 6

Example 1 was repeated except that 1000 ppm of polyacrylate, sodium was added to the system. The polyacrylate, sodium was poly(acrylic acid) sodium salt with an average Mw~2100.

Example 7

Example 1 was repeated except that 3000 ppm of polyacrylate, sodium was added to the system. The polyacrylate, sodium was poly(acrylic acid) sodium salt with an average Mw~2100.

Example 8

Example 1 was repeated except that 500 ppm of a surfactant was added to the system. The surfactant was an aqueous solution of mixture of an alkyldimethylamide, an alkylethersulfate, and an alkylphosphateester.

Example 9

Example 1 was repeated except that 1000 ppm of a surfactant was added to the system. The surfactant was an aqueous solution of mixture of an alkyldimethylamide, an alkylethersulfate, and an alkylphosphateester.

Example 10

Example 1 was repeated except that 250 ppm of hexamethylene diamine (HMD) was added to the system.

Example 11

Example 1 was repeated except that 500 ppm of 250 ppm of hexamethylene diamine (HMD) was added to the system.

Example 12

Example 1 was repeated except that 1000 ppm of 250 ppm of hexamethylene diamine (HMD) was added to the system.

Results of Examples 1-12 are summarized in Table 1. The data summarized in Table 1 represent evaluations of a number of additives for prevention of formation of stable emulsions and rags during catalyst extraction. Example 1 is a control experiment, which shows that in the absence of any additive a stable emulsion is formed. Examples 2-3 show that PEI is ineffective for preventing formation of a stable emulsion under these conditions. Example 4 shows that 1:1 polyethylenimine in water is ineffective for preventing stable emulsion formation at 500 ppm. By way of contrast, Example 5 shows that PEI/H$_2$O is effective at 1000 ppm for preventing stable emulsion formation. Examples 6-7 show that polyacrylate, sodium salt, is not effective at 1000 ppm, but is at 3000 ppm loading. Examples 8-9 show that the surfactant solution is not effective under any of the conditions evaluated for prevention of a stable emulsion. Examples 10-12 show that hexamethylene diamine is effective under these conditions for prevention of formation of a stable emulsion during catalyst extraction over the range of concentrations from 250-1000 ppm.

TABLE 1

Effectiveness of additives for prevention of stable emulsion formation during catalyst extraction

| Example | Additive | Concentration (ppm) | Stable emulsion |
|---|---|---|---|
| 1 | None | 0 | Yes |
| 2 | PEI | 500 | Yes |
| 3 | PEI | 1000 | Yes |
| 4 | PEI/H$_2$O (1:1) | 500 | Yes |
| 5 | PEI/H$_2$O (1:1) | 1000 | No |
| 6 | Polyacrylate, sodium | 1000 | Yes |
| 7 | Polyacrylate, sodium | 3000 | No |
| 8 | Surfactant | 500 | Yes |
| 9 | Surfactant | 1000 | Yes |
| 10 | HMD | 250 | No |
| 11 | HMD | 500 | No |
| 12 | HMD | 1000 | No |

A "No" in the column labeled Stable emulsion indicates that the additive was effective under the conditions tested for preventing the formation of a stable emulsion.

Examples 13-17

These Examples 13-17 illustrate that effective catalyst recovery occurs for a mononitrile to dinitrile ratio greater than 0.65.

Five different mixtures comprised of a Ni diphosphite complex, with the diphosphite ligand shown in Structure XX (where $R^{17}$ is isopropyl, $R^{18}$ is H, and $R^{19}$ is methyl), ZnCl$_2$ (equimolar with Ni) and differing in the ratio of mononitrile to dinitrile, were separately liquid-liquid batch extracted with an equal weight of cyane (i.e. cyclohexane). The molar ratio of organic mononitrile to organic dinitrile and the resulting extraction coefficients are shown in the Table 2 below. A compound may be effectively recovered if it has an extraction coefficient of 1 or greater at solvent to feed ratios greater than 1 using a countercurrent multistage extractor.

TABLE 2

Catalyst and ligand extraction coefficients for varying ratios of mononitriles-to-dinitriles

| Example | mononitrile/dinitrile | Catalyst extraction coefficient | Ligand extraction coefficient |
|---|---|---|---|
| 13 | 2.33 | 1.28 | 4.09 |
| 14 | 1.85 | 1.33 | 8.08 |
| 15 | 1.19 | 2.02 | 16.97 |
| 16 | 0.91 | 2.63 | 35.99 |
| 17 | 0.57 | 4.82 | 49.59 |

Example 18

This Example demonstrates the effect of hold-up time on the extractability of the diphosphite ligand catalyst.

A mixture comprised predominantly of organic dinitriles and a Ni diphosphite complex, the structure of the diphosphite ligand being shown in Structure XX (where $R^{17}$ is isopropyl, $R^{18}$ is H, and $R^{19}$ is methyl) and ZnCl$_2$ (equimolar with Ni) was divided into two portions. Both portions are liquid-liquid extracted in a three-stage contactor at 40° C., with an equal weight of cyclohexane. Both portions were sampled with time and the progress of the catalyst recovery into the extract phase is shown in Table 3 as the percent of the final steady state value achieved at a given time.

TABLE 3

Concentration of Diphosphite ligand with time in the extracting solvent phase.

| Time, minutes | % of steady state concentration at 40° C. |
|---|---|
| 2 | 12 |
| 4 | 19 |
| 8 | 34 |
| 14 | 52 |
| 30 | 78 |
| 60 | 100 |
| 91 | 100 |

Example 19

This Example illustrates the effect of temperature on the extractability of catalyst with first-stage extraction solvent recycle.

A mixture comprised predominantly of organic dinitriles and a Ni diphosphite complex, the structure of the diphosphite ligand being shown in Structure XXIV (where $R^{17}$ is methyl, $R^{18}$ is methyl and $R^{19}$ is H) and $ZnCl_2$ (equimolar with Ni) was divided into three portions. The portions were batch liquid-liquid extracted at 50° C., 65° C. and 80° C., respectively, with an equal weight of n-octane and monitored with time. The results are shown in Table 4.

TABLE 4

| Time | % of steady state at 50° C. | % of steady state at 65° C. | % of steady state at 80° C. |
|---|---|---|---|
| 2 | 0.0 | 0.0 | 1.8 |
| 4 | 0.0 | 0.0 | 1.6 |
| 8 | 0.0 | 0.0 | 3.6 |
| 14 | 0.0 | 0.0 | 4.3 |
| 20 | 0.0 | 0.0 | 3.6 |
| 30 | 0.0 | 0.0 | 7.6 |
| 60 | 0.0 | 1.6 | 16.3 |
| 90 | 0.7 | 4.0 | 48.6 |

Example 20

This Example demonstrates the effect of adding water in three-stage extraction with cyclohexane recycle in the first stage.

Fifteen grams of a mixture comprised predominantly of organic dinitriles and a Ni diphosphite complex, the structure of the diphosphite ligand being shown in Structure XXIV (where $R^{17}$ is methyl, $R^{18}$ is methyl and $R^{19}$ is H) and $ZnCl_2$ (equimolar with Ni), was extracted in a three-stage continuous extractor at a temperature of 50° C. with an equal weight of cyclohexane for one hour resulting in an catalyst extraction coefficient of 4.3, as measured by the amount of catalyst in the extract of the first stage divided by the amount of catalyst in the feed of the reaction mixture fed to the last stage of the three-stage countercurrent extractor.

To this mixture, 100 microliters of water was added. After continuing to heat and agitate for another hour, the diphosphite Ni extraction coefficient was measured as 13.4—a threefold increase.

Examples 21 and 22

These Examples demonstrate the effect of adding hexamethylene diamine (HMD) to the extraction zone.

Example 1 was repeated except that hexamethylene diamine was added to the product of a pentene-hydrocyanation reaction. In Example 21, 250 ppm of HMD was added, and in Example 22, 500 ppm of HMD was added. To a 50 mL, jacketed, glass laboratory extractor, equipped with a magnetic stirbar, digital stir-plate, and maintained at 65° C., was charged 10 grams of the product of pentene-hydrocyanation reactor product, and 10 grams of the extract from the second stage of a mixer-settler cascade, operated in counter-current flow.

The reactor product was approximately:
85% by weight $C_6$ dinitriles
14% by weight $C_5$ mononitriles
1% by weight catalyst components
360 ppm by weight active nickel.

The laboratory reactor was then mixed at 1160 rotations-per-minute, for 20 minutes, and then allowed to settle for 15 minutes. A stable emulsion was present throughout the extract phase in the absence of the addition of HMD. After 15 minutes of settling, essentially no emulsion phase was present when HMD was added. Samples were obtained of the extract and raffinate phases of the extractor and analyzed to determine the extent of catalyst extraction.

TABLE 5

Effect of hexamethylene diamine on catalyst extraction

| Example | Concentration of HMD added (ppm) | Catalyst recovery (KLL) | Stable emulsion |
|---|---|---|---|
| 1 | 0 | 14 | Yes |
| 21 | 250 | 43 | No |
| 22 | 500 | 80 | No |

What is claimed is:

1. A process for recovering diphosphite-containing compounds from a feed mixture comprising diphosphite-containing compounds, organic mononitriles, organic dinitriles and a Lewis acid in a multistage countercurrent liquid-liquid extractor with extraction solvent comprising aliphatic hydrocarbon, cycloaliphatic hydrocarbon or a mixture of aliphatic and cycloaliphatic hydrocarbon, said process comprising:
   a) flowing the feed mixture to a mixing section of a mixer-settler in the first stage of the multistage countercurrent liquid-liquid extractor;
   b) contacting the feed mixture with extraction solvent from the second stage of the multistage countercurrent liquid-liquid extractor in the mixing section of the mixer-settler of the first stage to form a mixed phase comprising a light phase and a heavy phase, wherein the light phase comprises extraction solvent and extracted diphosphite-containing compounds, and wherein the heavy phase comprises organic mononitrile and organic dinitriles;
   c) passing the mixture from step (b) to a settling section in the mixer-settler of the first stage, wherein the mixed phase separates into the light phase and the heavy phase; and
   d) introducing a Lewis base into the settling section of the first stage,
      wherein a complex of Lewis acid and Lewis base is formed in the settling section in the mixer-settler of the first stage, wherein at least a portion of the light phase is withdrawn from the settling section and treated to recover diphosphite-containing compounds extracted into the light phase, and wherein at least a portion of the heavy phase is passed to the second stage of the multistage countercurrent liquid-liquid extractor.

2. The process of claim 1, wherein the addition of Lewis base to the settling section of the first stage of the multistage countercurrent liquid-liquid extractor is sufficient to result in enhanced settling of the light phase and heavy phase in the settling section of the first stage.

3. The process of claim 1, wherein the addition of Lewis base to the settling section of the first stage of the multistage countercurrent liquid-liquid extractor is sufficient to achieve at least one of the following results: (a) a reduction in the size of an emulsion phase in the settling section, based upon the size of the emulsion phase in the absence of addition of Lewis base; (b) an increase in the rate of settling in the settling section, based upon the rate of settling in the absence of addition of Lewis base; (c) an increase in the amount of diphosphite-containing compounds in the light phase, based upon the upon the amount of diphosphite-containing compounds in the light phase in the absence of addition of Lewis base; (d) a reduction in the size of a rag layer in the settling section, based upon the size of a rag layer in the settling section in the absence of addition of Lewis base; and (e) reduction in the rate of formation of a rag layer in the settling section, based upon the rate of formation of a rag layer in the settling section in the absence of addition of Lewis base.

4. The process of claim 1, wherein the Lewis acid is $ZnCl_2$.

5. The process of claim 1, wherein the extraction solvent feed from the second stage comprises at least 1000 ppm of diphosphite-containing compounds.

6. A process according to claim 1 wherein the diphosphite-containing compound is a Ni complex with a diphosphite ligand selected from the group consisting of:

$(R^1O)_2P(OZO)P(OR^1)_2$,    I

II

III and
wherein in I, II and III, $R^1$ is phenyl, unsubstituted or substituted with one or more $C_1$ to $C_{12}$ alkyl or $C_1$ to $C_{12}$ alkoxy groups; or naphthyl, unsubstituted or substituted with one or more $C_1$ to $C_{12}$ alkyl or $C_1$ to $C_{12}$ alkoxy groups; and wherein Z and $Z^1$ are independently selected from the group consisting of structural formulae IV, V, VI, VII, and VIII:

IV

V and wherein
$R^2$, $R^3$, $R^4$, $R^5$, $R^6$, $R^7$, $R^8$, and $R^9$ are independently selected from the group consisting of H, $C_1$ to $C_{12}$ alkyl, and $C_1$ to $C_{12}$ alkoxy;
X is O, S, or $CH(R^{10})$;
$R^{10}$ is H or $C_1$ to $C_{12}$ alkyl;

VI

VII and wherein
$R^{11}$ and $R^{12}$ are independently selected from the group consisting of H, $C_1$ to $C_{12}$ alkyl, and $C_1$ to $C_{12}$ alkoxy and $CO_2R^{13}$,
$R^{13}$ is $C_1$ to $C_{12}$ alkyl, or $C_6$ to $C_{10}$ aryl unsubstituted or substituted with $C_1$ to $C_4$ alkyl;
Y is O, S, or $CH(R^{14})$;
$R^{14}$ is H or $C_1$ to $C_{12}$ alkyl;

VIII wherein
$R^{15}$ is selected from the group consisting of H, $C_1$ to $C_{12}$ alkyl, and $C_1$ to $C_{12}$ alkoxy and $CO_2R^{16}$,
$R^{16}$ is $C_1$ to $C_{12}$ alkyl, or $C_6$ to $C_{10}$ aryl, unsubstituted or substituted with $C_1$ to $C_4$ alkyl,
and wherein
for structural formulae I through VIII, the $C_1$ to $C_{12}$ alkyl, and $C_1$ to $C_{12}$ alkoxy groups may be straight chain or branched.

7. The process of claim 6, wherein at least a portion of the diphosphite-containing compound is complexed with zero valent Ni.

8. The process of claim 1 wherein at least one stage of the extraction is carried out above 40° C.

9. The process of claim 1 wherein the Lewis base is a monodentate triarylphosphite wherein the aryl groups are unsubstituted or substituted with alkyl groups having 1 to 12 carbon atoms, and wherein the aryl groups may be interconnected.

10. The process of claim 9 wherein the Lewis base is selected from the group consisting of:
   a) anhydrous ammonia, pyridine, alkylamine, dialkylamine, trialkylamine wherein the alkyl groups have 1 to 12 carbon atoms; and
   b) polyamine; and
   c) poly(acrylic acid), sodium salt.

11. The process of claim 10, wherein the polyamine comprises at least one selected from hexamethylene diamine and dimers and trimers of hexamethylene diamine.

12. The process of claim 10, wherein the polyamine comprises at least one selected from polyethylenimine, and polyethylenimine in aqueous solution.

13. The process of claim 10, wherein the polyamine comprises dimers of hexamethylene diamine.

14. The process of claim 10, wherein the Lewis base compound is Amberlyst 21® resin.

15. The process of claim 1, wherein the extraction solvent is cyclohexane.

16. The process of claim 1, wherein the feed mixture is an effluent stream from a hydrocyanation process.

17. The process of claim 15, wherein the hydrocyanation process includes a 3-pentenenitrile hydrocyanation process.

18. The process of claim 15, wherein the hydrocyanation process includes a 1,3-butadiene hydrocyanation process.

* * * * *